US011191954B2

(12) United States Patent
Marnfeldt et al.

(10) Patent No.: US 11,191,954 B2
(45) Date of Patent: Dec. 7, 2021

(54) SYSTEMS AND METHODS FOR PROGRAMMING NEUROMODULATION WAVEFORM

(71) Applicant: Boston Scientific Neuromodulation Corporation, Valencia, CA (US)

(72) Inventors: Goran N. Marnfeldt, Valencia, CA (US); Michael A. Moffitt, Solon, OH (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 138 days.

(21) Appl. No.: 16/556,730

(22) Filed: Aug. 30, 2019

(65) Prior Publication Data

US 2020/0101284 A1 Apr. 2, 2020

Related U.S. Application Data

(63) Continuation of application No. 15/790,977, filed on Oct. 23, 2017, now Pat. No. 10,441,781.

(60) Provisional application No. 62/425,855, filed on Nov. 23, 2016.

(51) Int. Cl.
*A61N 1/36* (2006.01)
*A61N 1/05* (2006.01)
*A61N 1/372* (2006.01)

(52) U.S. Cl.
CPC ....... *A61N 1/0551* (2013.01); *A61N 1/36062* (2017.08); *A61N 1/36071* (2013.01);
(Continued)

(58) Field of Classification Search
CPC .............. A61N 1/0551; A61N 1/36062; A61N 1/36071; A61N 1/36114; A61N 1/36146; A61N 1/37235
See application file for complete search history.

(56) References Cited

U.S. PATENT DOCUMENTS 7,650,184 B2 1/2010 Walter
8,019,439 B2 9/2011 Kuzma et al.
(Continued)

FOREIGN PATENT DOCUMENTS

WO WO-2018097917 A1 5/2018
WO WO-2018097918 A1 5/2018

OTHER PUBLICATIONS

"U.S. Appl. No. 15/790,977, Non Final Office Action dated Feb. 20, 2019", 10 pgs.
(Continued)

*Primary Examiner* — George Manuel
(74) *Attorney, Agent, or Firm* — Schwegman Lundberg & Woessner, P.A.

(57) ABSTRACT

This document discusses, among other things, systems and methods for programming neuromodulation therapy to treat neurological or cardiovascular diseases. A system includes an input circuit that receives a modulation magnitude representing a level of stimulation intensity, a memory that stores a plurality of gain functions associated with a plurality of modulation parameters, and a electrostimulator that may generate and deliver an electrostimulation therapy. A controller may program the electrostimulator with the plurality of modulation parameters based on the received modulation magnitude and the plurality of gain functions, and control the electrostimulator to generate electrostimulation therapy according to the plurality of modulation parameters.

20 Claims, 7 Drawing Sheets

(52) U.S. Cl.
CPC ...... *A61N 1/36114* (2013.01); *A61N 1/36146* (2013.01); *A61N 1/37235* (2013.01)

(56) References Cited

U.S. PATENT DOCUMENTS

| | | | |
|---|---|---|---|
| 9,358,396 | B2 | 6/2016 | Holley |
| 10,441,781 | B2 | 10/2019 | Marnfeldt et al. |
| 10,617,872 | B2 | 4/2020 | Marnfeldt |
| 2001/0007950 | A1 | 7/2001 | North et al. |
| 2004/0249416 | A1* | 12/2004 | Yun ............. A61N 1/36017 607/2 |
| 2012/0197336 | A1 | 8/2012 | Su |
| 2014/0277267 | A1 | 9/2014 | Vansickle et al. |
| 2015/0032181 | A1 | 1/2015 | Baynham et al. |
| 2015/0165202 | A1 | 6/2015 | Grandhe |
| 2015/0217116 | A1 | 8/2015 | Parramon et al. |
| 2016/0082252 | A1 | 3/2016 | Hershey et al. |
| 2016/0303376 | A1 | 10/2016 | Dinsmoor et al. |
| 2017/0173335 | A1 | 6/2017 | Min et al. |
| 2018/0140830 | A1 | 5/2018 | Marnfeldt et al. |
| 2018/0140845 | A1 | 5/2018 | Marnfeldt |

OTHER PUBLICATIONS

"U.S. Appl. No. 15/790,977, Notice of Allowance dated Jun. 12, 2019", 7 pgs.
"U.S. Appl. No. 15/790,977, Response filed May 13, 2019 to Non Final Office Action dated Feb. 20, 2019", 10 pgs.
"International Application Serial No. PCT/US2017/057851, International Search Report dated Feb. 16, 2018", 4 pgs.
"International Application Serial No. PCT/US2017/057851, Written Opinion dated Feb. 16, 2018", 6 pgs.
"International Application Serial No. PCT/US2017/057912, International Search Report dated Feb. 16, 2018", 5 pgs.
"International Application Serial No. PCT/US2017/057912, Written Opinion dated Feb. 16, 2018", 8 pgs.
"U.S. Appl. No. 15/790,642, Examiner Interview Summary dated Sep. 30, 2019", 3 pgs.
"U.S. Appl. No. 15/790,642, Non Final Office Action dated Aug. 22, 2019", 10 pgs.
"U.S. Appl. No. 15/790,642, Notice of Allowance dated Dec. 13, 2019", 7 pgs.
"U.S. Appl. No. 15/790,642, Response filed Nov. 20, 2019 to Non Final Office Action dated Aug. 22, 2019", 10 pgs.
"European Application Serial No. 17794562.3, Response to Communication Pursuant to Rules 161 & 162 filed Jan. 17, 2020", 9 pgs.
"European Application Serial No. 17794573.0, Response to Communication Pursuant to Rules 161 & 162 filed Jan. 17, 2020", 9 pgs.
"International Application Serial No. PCT/US2017/057851, International Preliminary Report on Patentability dated Jun. 6, 2019", 8 pgs.
"International Application Serial No. PCT/US2017/057912, International Preliminary Report on Patentability dated Jun. 6, 2019", 8 pgs.

\* cited by examiner

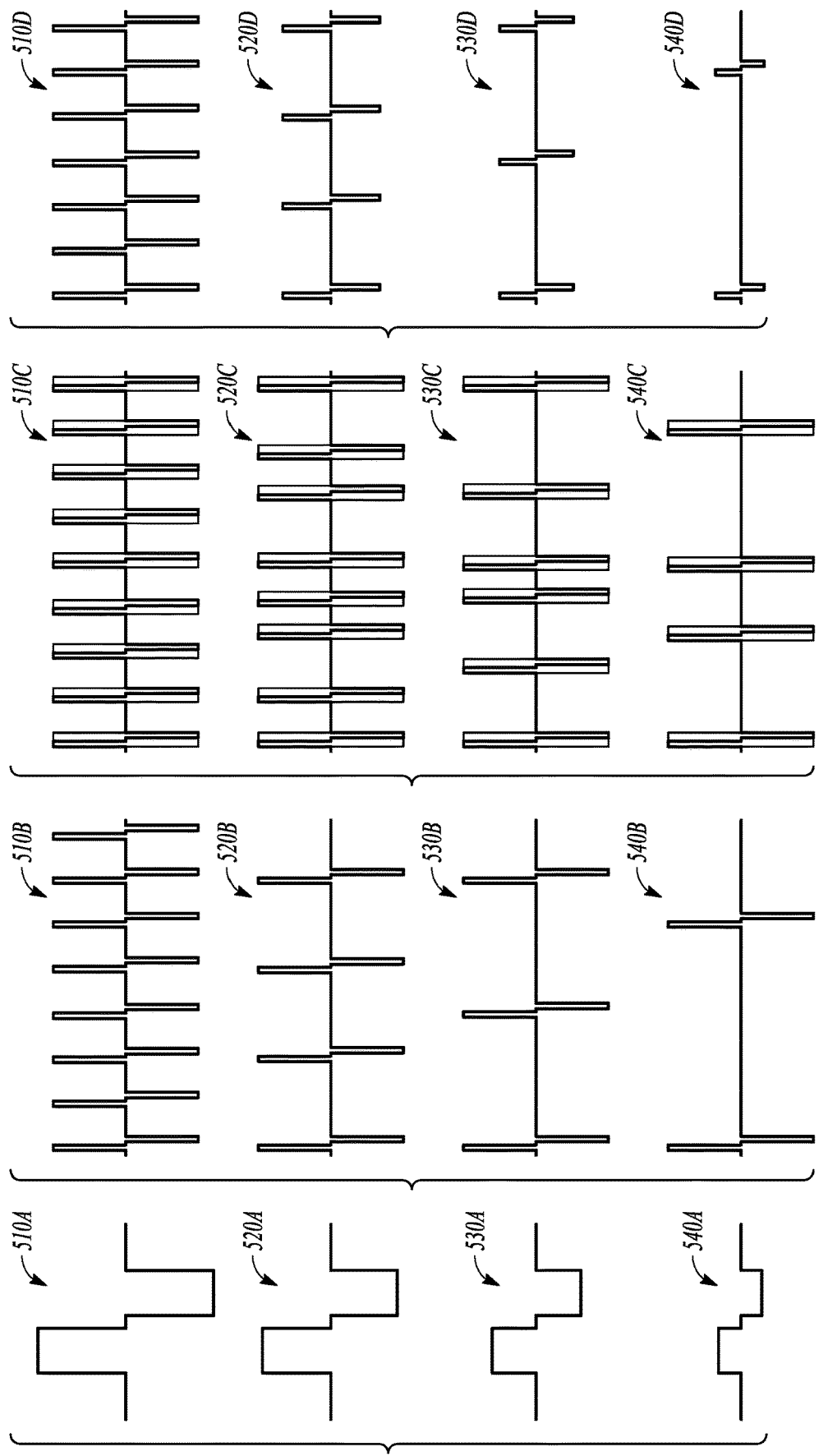

SYSTEMS AND METHODS FOR PROGRAMMING NEUROMODULATION WAVEFORM

CLAIM OF PRIORITY

This application is a continuation of U.S. application Ser. No. 15/790,977, filed Oct. 23, 2017, which claims the benefit of priority under 35 U.S.C. § 119(e) of U.S. Provisional Patent Application Ser. No. 62/425,855, filed on Nov. 23, 2016, each of which is herein incorporated by reference in its entirety.

CROSS-REFERENCE TO RELATED APPLICATIONS

This application is related to commonly assigned U.S. Provisional Patent Application Ser. No. 62/425,848, entitled "SYSTEMS AND METHODS FOR PROGRAMMING A NEUROMODULATION THERAPY", filed on Nov. 23, 2016, which is incorporated herein by reference in their entirety.

TECHNICAL FIELD

This document relates generally to medical systems, and more particularly, but not by way of limitation, to systems, devices, and methods for programming neuromodulation waveform.

BACKGROUND

Neuromodulation, also referred to as neurostimulation, has been proposed as a therapy for a number of conditions. Examples of neuromodulation include Spinal Cord Stimulation (SCS), Deep Brain Stimulation (DBS), Peripheral Nerve Stimulation (PNS), and Functional Electrical Stimulation (FES). For example, SCS has been used to treat chronic pain syndromes. Some neural targets may be complex structures with different types of nerve fibers. An example of such a complex structure is the neuronal elements in and around the spinal cord targeted by SCS.

Implantable neuromodulation systems have been applied to deliver such a therapy. An implantable neuromodulation system may include an implantable neuromodulator, also referred to as an implantable pulse generator (IPG), and one or more implantable leads each including one or more electrodes. The implantable neuromodulator delivers neuromodulation energy through one or more electrodes placed on or near a target site in the nervous system. An external programming device may be used to program the implantable neuromodulator with stimulation parameters controlling the delivery of the neuromodulation energy.

Electrical stimulation energy may be delivered from the implantable neuromodulator to the electrodes to stimulate neural tissue in the form of an electrical pulsed waveform. The configuration of electrodes used to deliver electrical pulses to the targeted tissue constitutes an electrode configuration, with the electrodes capable of being selectively programmed to act as anodes (positive), cathodes (negative), or left off (zero). In other words, an electrode configuration represents the polarity being positive, negative, or zero. Other parameters that may be controlled or varied include the amplitude, pulse width, and rate (or frequency) of the electrical pulses provided through the electrode array. Each electrode configuration, along with the electrical pulse parameters, constitutes a modulation parameter set for use in an electrostimulation therapy.

SUMMARY

Programming of neuromodulation therapy, such as SCS, conventionally involves separate and independent programming of each of a multitude of modulation parameters such as parameters that define a modulation waveform. Modulation parameters are conventionally programmed in a linear fashion such that the stimulation energy delivered to the tissue is linearly proportional to the current or voltage amplitude of a stimulation pulse. However, some biological systems may demonstrate a nonlinear response to electrostimulation. For example, when the electrostimulation energy is below a particular threshold, no physiological response would be induced. However, when electrostimulation energy exceeds another threshold, unwanted side effects such as pain may occur. Additionally, some neuromodulation systems may include electrostimulation configuration and complex modulation waveforms. These modulation waveforms may be characterized by a large amount of modulation parameters. Programming of the neuromodulation therapy may require adjusting these modulation parameters individually and separately, and transmitting the modulation parameters to an IPG. This may put a burden on a telemetry system that enables communications between the IPG and the programming device. The present inventors have recognized that there remains a demand for improved systems and methods to program an electrostimulation system for delivering electrostimulation therapy, particularly to more efficiently program neuromodulation waveform.

Example 1 is a system for providing electrostimulation to a patient. The system comprises an input circuit configured to receive information corresponding to a user input of a modulation magnitude representing a level of stimulation intensity, a memory configured to store a plurality of gain functions associated with a plurality of modulation parameters, an electrostimulator configured to generate an electrostimulation therapy for delivery to the patient, and a controller. The plurality of gain functions each defines a correspondence between values of a modulation parameter and a plurality of modulation magnitudes. The controller may program the electrostimulator with the plurality of modulation parameters based on the received modulation magnitude and the plurality of gain functions, and control the electrostimulator to elicit the electrostimulation therapy according to the plurality of modulation parameters.

In Example 2, the subject matter of Example 1 optionally includes the input circuit that may be configure to receive the modulation magnitude within a magnitude range based on a perception threshold.

In Example 3, the subject matter of Example 2 optionally includes the magnitude range that is further based on a maximum tolerable threshold.

In Example 4, the subject matter of any one or more of Examples 1-3 optionally includes a modulation magnitude equalizer that may produce a plurality of modulation magnitudes representing a plurality of levels of stimulation intensity within a specific range.

In Example 5, the subject matter of any one or more of Examples 1-4 optionally includes the electrostimulator that is further configured to generate a spinal cord stimulation (SCS) therapy or a deep brain stimulation therapy.

In Example 6, the subject matter of any one or more of Examples 1-5 optionally includes the electrostimulator that is further configured to generate a cardiac or neural stimulation therapy to treat a cardiovascular disease.

In Example 7, the subject matter of any one or more of Examples 1-6 optionally includes the plurality of gain functions that are associated with a plurality of temporal modulation parameters comprising at least one of a pulse amplitude; a pulse width; a pulse frequency; or a burst intensity.

In Example 8, the subject matter of any one or more of Examples 1-7 optionally includes the plurality of gain functions that are associated with a plurality of morphological modulation parameters respectively defining one or more portions of a stimulation waveform morphology.

In Example 9, the subject matter of Example 8 optionally includes the plurality of morphological modulation parameters that may include morphologies of at least first and second pulses of a multiphasic stimulation waveform. The plurality of gain functions comprise a first gain function defining a modulation parameter of the first pulse at various modulation magnitudes, and a second gain function defining a modulation parameter of the second pulse at various modulation magnitudes.

In Example 10, the subject matter of any one or more of Examples 1-9 optionally includes the plurality of gain functions that are associated with a plurality of spatial modulation parameters including selected active electrodes and stimulation energy fractionalization over the selected active electrodes.

In Example 11, the subject matter of any one or more of Examples 1-10 optionally includes: the modulation magnitude that corresponds to a user input for selecting a first modulation program or deselecting a second modulation program, wherein the first and second modulation programs each includes an aggregation of respective plurality of modulation parameters; and the controller that may be configured to (a) program the electrostimulator with the selected first modulation program, and to control the electrostimulator to elicit the electrostimulation therapy according to the selected first modulation program, or (b) to withhold the electrostimulation therapy according to the deselected second modulation program.

In Example 12, the subject matter of Example 11 optionally includes the modulation magnitude corresponds to a user input for selecting a modulation program associated with a physiological state or a physical activity. The modulation program may comprise at least one of: a modulation program for sleep state; a modulation program for awakening state; or a modulation program for a specific physical activity level.

In Example 13, the subject matter of any one or more of Examples 1-12 optionally includes the plurality of gain functions that may include linear, piece-wise linear, or non-linear functions of the modulation magnitude.

In Example 14, the subject matter of any one or more of Examples 1-13 optionally further includes an ambulatory medical device (AMD) that includes at least a portion of one or more of the electrostimulator or the controller, and an external programmer device configured to be communicatively coupled to the AMD. The external programmer device may include at least a portion of the memory.

In Example 15, the subject matter of any one or more of Example 1-14 optionally includes the modulation magnitude relative to a baseline electrophysiological measurement.

Example 16 is a system for providing electrostimulation to a patient. The system comprises an input circuit configured to receive information corresponding to a user input of at least first and second modulation magnitudes each representing a level of stimulation intensity. The first modulation magnitude may be represented as a value relative to a baseline electrophysiological measurement, and the second modulation magnitude may be represented as a value relative to a perception threshold. The system comprises a memory configured to store a plurality of gain functions associated with a plurality of modulation parameters, an electrostimulator configured to generate an electrostimulation therapy for delivery to the patient, and a controller. The plurality of gain functions each defines a correspondence between values of a modulation parameter and a plurality of modulation magnitudes. The controller may program the electrostimulator with the plurality of modulation parameters based on the received modulation magnitude and the plurality of gain functions, and control the electrostimulator to elicit the electrostimulation therapy including a sub-perception stimulation according to the first modulation magnitude and a supra-perception stimulation according to the second modulation magnitude.

Example 17 is a method for providing electrostimulation to a patient via an ambulatory medical device (AMD) communicatively coupled to an external programmer device. The method comprises steps of: receiving information corresponding to a user input of a modulation magnitude representing a level of stimulation intensity; establishing a plurality of gain functions associated with a plurality of modulation parameters, the plurality of gain functions each defining a correspondence between values of a modulation parameter and a plurality of modulation magnitudes; determine values for the plurality of modulation parameters using the received modulation magnitude and the plurality of gain functions; programming the plurality of modulation parameters, via the external programmer device, with the determined values; and generating the electrostimulation therapy, via the AMD, according to the plurality of modulation parameters.

In Example 18, the subject matter of Example 17 optionally includes the received modulation magnitude that is within a magnitude range based on one or more of a perception threshold or a maximum tolerable threshold.

In Example 19, the subject matter of any one or more of Examples 17-18 optionally includes generating at least one of a spinal cord stimulation (SCS) therapy, a deep brain stimulation therapy, or a cardiac or neural stimulation therapy.

In Example 20, the subject matter of any one or more of Examples 17-19 optionally includes establishing gain functions associated with a plurality of temporal modulation parameters comprising at least one of: a pulse amplitude; a pulse width; a pulse frequency; or a burst intensity.

In Example 21, the subject matter of any one or more of Examples 17-20 optionally includes establishing the gain functions associated with a plurality of morphological modulation parameters respectively defining one or more portions of stimulation waveform morphology.

In Example 22, the subject matter of any one or more of Examples 17-21 optionally includes establishing the gain functions associated with a plurality of spatial modulation parameters including selected active electrodes and stimulation energy fractionalization over the selected active electrodes.

In Example 23, the subject matter of any one or more of Examples 17-22 optionally includes steps of receiving a modulation magnitude that corresponds to a user input for selecting a first modulation program or deselecting a second modulation program, the first and second modulation programs each including an aggregation of respective plurality of modulation parameters. The plurality of modulation parameters correspond to the selected first modulation program. The electrostimulation therapy may include generating an electrostimulation therapy according to the selected first modulation program, or withholding the electrostimulation therapy according to the deselected second modulation program.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 5A-5D illustrates, by way of example and not limitation, temporal modulation parameters as controlled by the modulation magnitude and the resulting electrostimulation waveforms.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is based on the appended claims and their legal equivalents.

Advancements in neuroscience and neuromodulation research have led to a demand for using complex and/or individually optimized patterns of neuromodulation energy for various types of therapies. Disclosed herein are systems, devices, and methods for programming neuromodulation therapy to treat neurological or cardiovascular diseases. A system may include an input circuit that may receive a modulation magnitude representing a level of stimulation intensity, a memory that stores a plurality of gain functions associated with a plurality of modulation parameters, and an electrostimulator that may generate an electrostimulation therapy. A controller may program the electrostimulator with the plurality of modulation parameters based on the received modulation magnitude and the plurality of gain functions, and control the electrostimulator to generate electrostimulation therapy according to the plurality of modulation parameters.

The present system may be implemented using a combination of hardware and software designed to provide a closed-loop pain management regime to increase therapeutic efficacy, increase patient satisfaction for neurostimulation therapies, reduce side effects, and/or increase device longevity. The present system may be applied in any neurostimulation (neuromodulation) therapies, including but not limited to SCS, DBS, PNS, FES, and Vagus Nerve Stimulation (VNS) therapies. With a modulation magnitude that controls multiple modulation parameters concurrently, the present system is advantageous in reducing telemetry system's burden and saving on the communication bandwidth between the IPG and the programming device, and simplifying the patient's interaction with their device such as for programming neuromodulation therapy.

Figure 1:
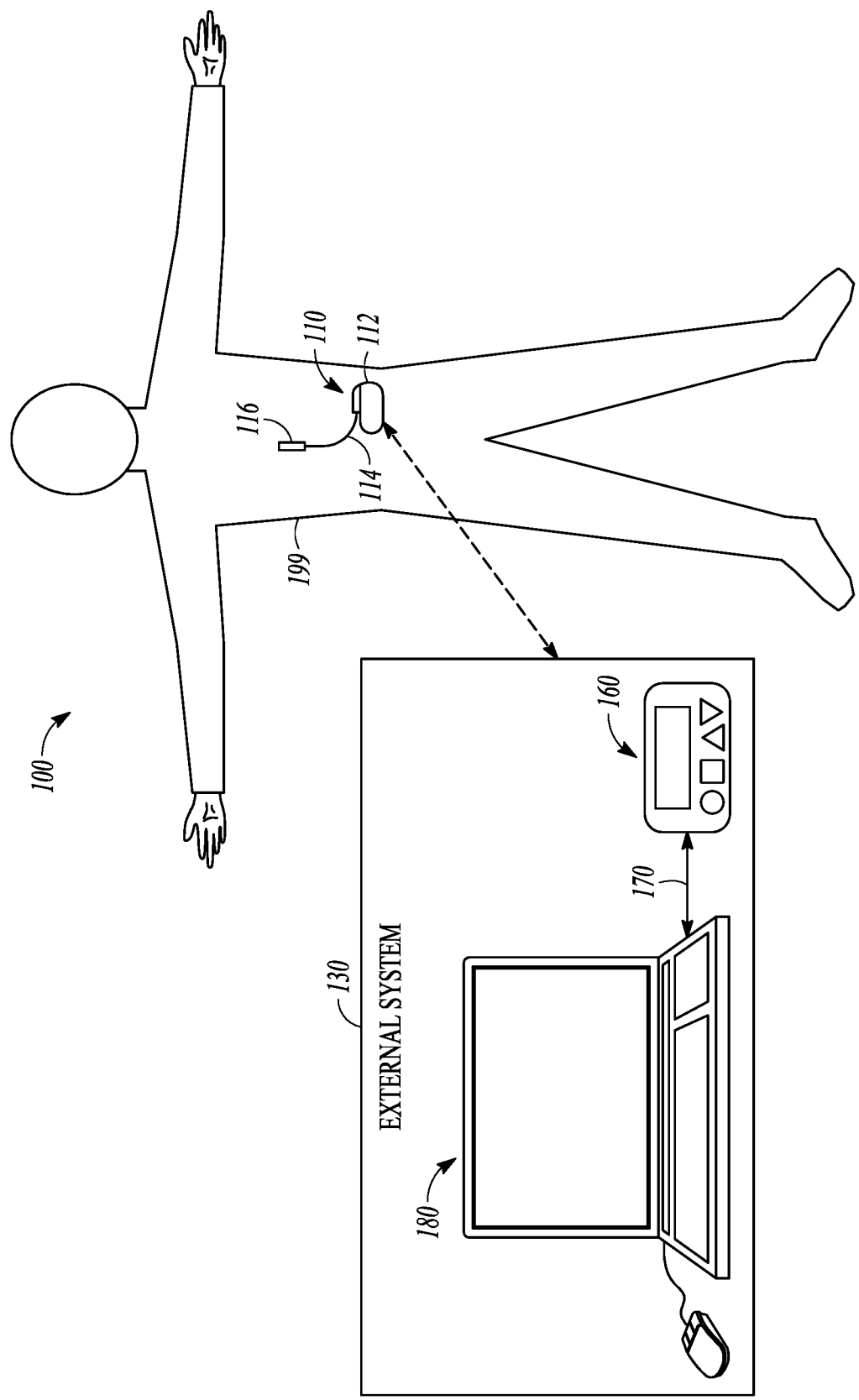
FIG. 1 illustrates, by way of example and not limitation, a neuromodulation system and portions of an environment in which the neuromodulation system may operate.

FIG. 1 illustrates, by way of example and not limitation, a neuromodulation system 100 and portions of an environment in which the neuromodulation system 100 may operate. The neuromodulation system 100 may include an ambulatory system 110 and an external system 130 in communication with the ambulatory system 110 via a communication link 120.

The ambulatory system 110, configured to be associated with a body 199 of a patient, may include an ambulatory device such as an implantable medical device (IMD) 112, a lead system 114, and one or more electrodes 116. The 112 may be configured to generate one or more energy modalities for delivery to target tissues for medical diagnosis, or to achieve desired therapeutic effects such as to modify, restore, or improve neural or cardiac function. Examples of the energy modalities may include electrical, magnetic, or other forms of energy.

In an example, the IMD 112 may include a hermetically sealed can, which houses sensing circuitry, electrostimulation circuitry, control circuitry, communication circuitry, and a battery, among other components. The sensing circuitry of the IMD 112 may sense physiological or functional signals from the patient via electrodes 116 or various types of ambulatory sensors associated with the patient. The sensing electrodes or the ambulatory sensors may be included within, or otherwise in wired or wireless connection with, the IMD 112. In an example, the IMD 112 may be an implantable neuromodulator device (IND) configured to provide SCS, DBS, PNS, or other types of neuromodulation therapies. The electrostimulation circuitry may generate electrostimulation pulses to stimulate a neural target via the electrodes 116. In an example, the electrodes 116 may be positioned on or near a spinal cord, and the electrostimulation circuitry may be configured to deliver SCS to treat pain or other disorders. In another example, the electrodes 116 may be surgically placed at other neural targets such as a brain or a peripheral neutral tissue, and the electrostimulation circuitry may be configured to deliver brain or peripheral stimulation to treat epilepsy, chronic pain, obsessive compulsive disorder, tremor, Parkinson's disease, or dystonia, among other movement and affective disorders. The IMD 112 may additionally or alternatively include an implantable cardiac device coupled to electrodes positioned at a target cardiovascular tissue or a target neural tissue, and the IMD 112 may sense cardiac activities or generate a cardiac or neural stimulation therapy to treat a cardiovascular disease.

In various examples, the electrodes 116 may be distributed in one or more leads of the lead system 114 electrically coupled to the 112. In an example, the lead system 114 may include a directional lead that includes at least some segmented electrodes circumferentially disposed about the directional lead. Two or more segmented electrodes may be distributed along a circumference of the lead. The actual number and shape of leads and electrodes may vary according to the intended application. Detailed description of construction and method of manufacturing percutaneous stimulation leads are disclosed in U.S. Pat. No. 8,019,439, entitled "Lead Assembly and Method of Making Same," and U.S. Pat. No. 7,650,184, entitled "Cylindrical Multi-Contact Electrode Lead for Neural Stimulation and Method of Making Same," the disclosures of which are incorporated herein by reference. The electrodes 116 may provide an electrically conductive contact providing for an electrical interface between the IMD 112 and tissue of the patient. The neuromodulation pulses are each delivered from the IMD 112 through a set of electrodes selected from the electrodes 116. The selected electrodes may form electrode combinations which define the electrodes that are activated as anodes (positive cathodes (negative), and turned off (zero). Stimulation energy may be fractionalized over the selected active electrodes by defining amount of current, voltage, or energy assigned to the active electrodes. In various examples, multiple individually defined pulses may be included in a neuromodulation waveform, and the set of electrodes may be individually definable by the user for each of the individually defined pulses.

Although the discussion herein with respect to the neuromodulation system 100 focuses on implantable device such as the IMD 112, this is meant only by way of example and not limitation. It is within the contemplation of the inventors and within the scope of this document, that the systems, devices, and methods discussed herein may also be used for programming modulation waveform and neuromodulation therapy via subcutaneous medical devices, wearable medical devices, or other external medical devices, or a combination of implantable, wearable, or other external devices.

The external system 130, via a communication link 120, may control the operation of the IMD 112, including programming the IMD 112 with neuromodulation therapies or cardiac therapies. The external system 130 may additionally receive, via the communication link 120, information acquired by the IMD 112, such as one or more physiological or functional signals. In an example, the external system 130 may characterize pain sensed by a patient using the physiological or functional signals received from the IMD 112, and program the IMD 112 to deliver pain therapy in a closed-loop fashion based at least on the pain characterization.

The communication link 120 may include one or more communication channels and intermediate devices between the external system and the IMD, such as a wired link, a telecommunication link such as an Internet connection, or a wireless link such as one or more of an inductive telemetry link, a radio-frequency (RF) telemetry link. The communication link 120 may provide for data transmission between the IMD 112 and the external system 130. The transmitted data may include, for example, real-time physiological data acquired by the IMD 112, physiological data acquired by and stored in the IMD 112, therapy history data, data indicating device operational status of the IMD 112, one or more programming instructions to the IMD 112 which may include configurations for sensing physiologic signal or stimulation commands and stimulation parameters, or device self-diagnostic test, among others.

The external system 130 may include a dedicated hardware/software system such as a programmer, a remote server-based patient management system, or alternatively a system defined predominantly by software running on a standard personal computer. By way of example and not limitation, and as illustrated in FIG. 1, the external system 130 may include a programmer 180 and an intermediate controller 160. The programmer 180 may be communicatively coupled to the IMD 112, such as via a RF telemetry link (not shown). The programmer 180 may present to a system user, such as a clinician, neuromodulation parameters for programming the IMD 112, and enable the system user to program the IMD 112 using the neuromodulation parameters. Such neuromodulation parameters may include electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (which may be measured in milliamps or volts depending on whether the IMD 112 supplies constant current or constant voltage to the electrodes 140), pulse duration (which may be measured in microseconds), pulse rate (measured in pulses per second), and burst intensity (which may be measured as the stimulation on duration X and stimulation off duration Y). The programming of the IMD 112 may be performed intraoperatively (e.g., during implant of the IMD 112 and/or the leads 130 in an operating room) or during a follow-up visit with the patient.

The programmer 180 may alternatively indirectly communicate with the IMD 112 through the intermediate controller 160. The intermediate controller 160 may take the form of a handheld external remote control (RC) device configured to be in communication with the IMD 112 via a bi-directional communications link, such as a RF telemetry. A system user, such as the patient, may operate the RC 260 to remotely instruct the IMD 112 to generate electrical stimulation pulses in accordance with the stimulation parameters produced by the external system 130. The programmer 180 may communicate with the RC 260 via an infrared communications link 170. The neuromodulation parameters provided by the programmer 180 may also be used to program the RC 260, so that the neuromodulation parameters may be subsequently modified by operation of the RC 260 in without the assistance of the programmer 180. In an example, the programmer 180, either alone or in combination with the RC 260, may control the operation of the IMD 112, such as turning on or off and programming the IMD 112 with different neuromodulation parameter sets to actively control the characteristics of the electrical modulation energy output by the IMD 112.

Portions of the IMD 112 or the external system 130 may be implemented using hardware, software, firmware, or combinations thereof. Portions of the IMD 112 or the external system 130 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, or a portion thereof. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
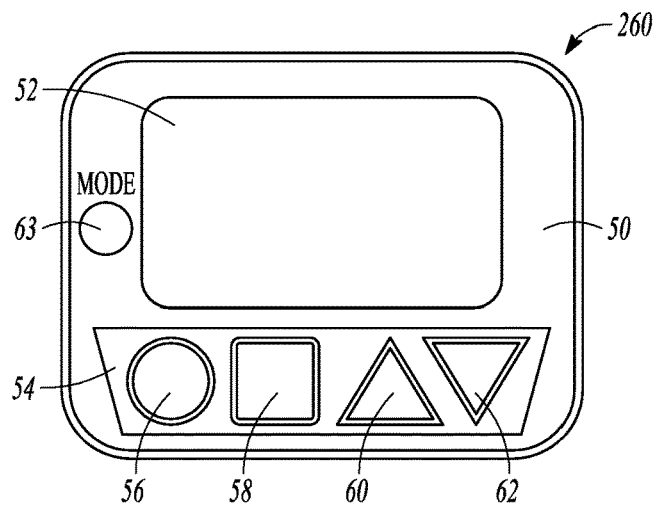
FIG. 2 illustrates, by way of example and not limitation, an external remote controller (RC) that telemetrically controls the IMD.

FIG. 2 illustrates, by way of example and not limitation, an external remote controller (RC) 260 that may telemetrically control the IMD 112. The RC 260, which is an embodiment of the intermediate controller 160, may allow a patient to adjust specific aspects of the neuromodulation therapy in an ambulatory setting. The RC 260 comprises a casing 50 for housing internal circuitry, a display screen 52, and button pad 54 carried by the exterior of the casing 50. In the illustrated embodiment, the display screen 52 may include a lighted flat panel display screen, and the button pad 54 may comprise a membrane switch with metal domes positioned over a flex circuit, and a keypad connector connected directly to the internal circuitry of the RC 260. In an example, the display screen 52 may include a touchscreen. Further details of the functionality and internal components of the RC 260 are discussed in U.S. Pat. No. 6,895,280, the disclosures of which are incorporated herein by reference.

The button pad 54 may include buttons 56, 58, 60, and 62. In the non-limiting example as illustrated in FIG. 2, the button 56 serves as an ON/OFF button that may be actuated to turn the 112 ON or OFF. The button 58 serves as a select button that may be actuated to switch the RC 260 between screen displays and/or parameters. The buttons 60 and 62 may provide for setting or adjustment of modulation parameters within the IMD 112. The buttons 60 and 62 serve as up/down buttons that may be actuated to increment or decrement any of modulation parameters of the pulsed electrical train generated by the IMD 112, including pulse amplitude, pulse width, or pulse rate, among other modulation parameters. In various examples, the selection button 58 may be actuated to place the RC 260 in a Pulse Amplitude Adjustment Mode, during which the pulse amplitude may be adjusted via the up/down buttons 60 and 62, a Pulse Width Adjustment Mode, during which the pulse width may be adjusted via the up/down buttons 60 and 62, or a Pulse Rate Adjustment Mode, during which the pulse rate may be adjusted via the up/down buttons 60 and 62.

In an example, the selection button 58 may be actuated to place the RC 260 in a Modulation Magnitude Adjustment Mode. The modulation magnitude, which may take a unitless value, represents a level of stimulation intensity. Compared to the Pulse Amplitude Adjustment Mode, the Pulse Width Adjustment Mode, or the Pulse Rate Adjustment Mode, which provide for individualized and independent adjustment of one particular modulation parameter (such as pulse amplitude, pulse width, or pulse rate, respectively), during the Modulation Magnitude Adjustment Mode, two or more modulation parameters may be concurrently adjusted using a single modulation magnitude. The modulation magnitude may be increased or decreased via the up/down buttons 60 and 62. For example, when the button 60 is actuated to increase the modulation magnitude, two or more of the pulse amplitude, pulse width, pulse rate, or burst intensity, among other modulation parameters, may be concurrently adjusted. Other types of actuators other than the up/down buttons 60 and 62, such as a dial, slider bar, or keypad, may be used to increment or decrement the modulation parameter.

A single modulation magnitude may control multiple modulation parameters according to respective parameter gain functions (PGFs) that associate the modulation parameters with the modulation magnitudes. The PGFs may be created and stored in a memory. The PGFs may be linear, piece-wise linear, or nonlinear functions of modulation magnitude, and the modulation parameters may accordingly be linearly or nonlinearly controlled by the modulation magnitude. For example, when the PGFs are linear or nonlinear growth functions, an increase in the modulation magnitude may produce a proportionally stronger perceived modulation effect. Examples of the RC 260 running in the Modulation Magnitude Adjustment Mode and the adjustment of the modulation magnitude are discussed below, such as with reference to FIGS. 4-6.

The RC 260 may additionally include an optional modulation selection control element 63 that allows the user to select between different modes. The modulation selection control element 63 may take the form of a button, a touchscreen icon, or other types of acutators. The modulation selection control element 63 may be repeatedly actuated to toggle the IMD 112 between the super-threshold, subthreshold, and hybrid delivery modes. For example, the modulation selection control element 63 may be actuated once to switch the IMD 112 from the super-threshold delivery mode to the sub-threshold delivery mode, actuated once again to switch the IMD 112 from the sub-threshold delivery mode to the hybrid delivery mode, actuated once again to switch the IMD 112 from the hybrid delivery mode back to the super-threshold delivery mode, and so forth. The order of the mode selection may be changed. For example, the modulation selection control element 63 may be actuated once to switch the IMD 112 from the sub-threshold delivery mode to the super-threshold delivery mode, actuated once again to switch the IMD 112 from the super-threshold delivery mode to the hybrid delivery mode, actuated once again to switch the IMD 112 from the hybrid delivery mode back to the sub-threshold delivery mode, and so forth. Each of the modulation delivery modes may be selected by toggling the modulation selection control element 63.

Figure 3A:
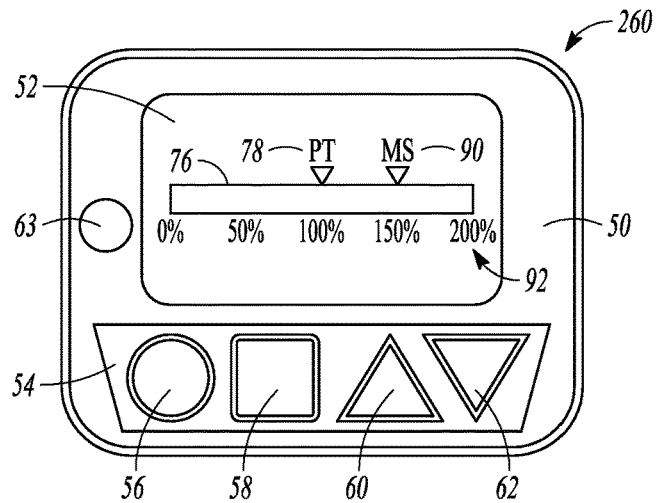
FIGS. 3A-3B illustrate, by way of example and not limitation, various examples of an intermediate controller that may be used by a user to control the generation of the modulation waveform.
Figure 3B:
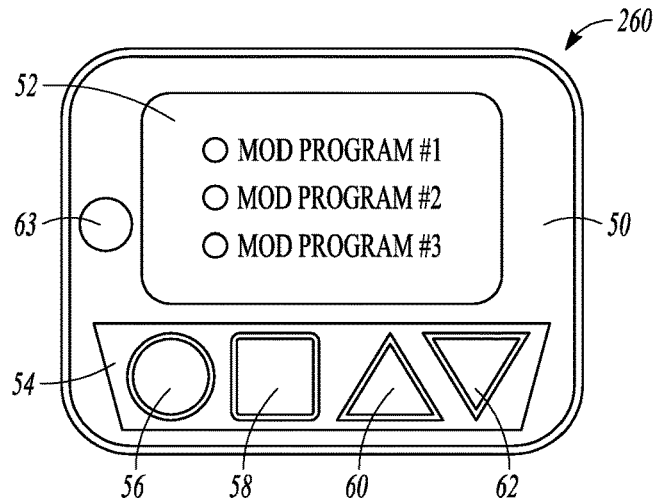

FIGS. 3A-3B illustrate, by way of example and not limitation, various examples of an intermediate controller that may be used by a user to control the generation of the modulation waveform. FIG. 3A illustrates an RC 260 that may be programmed to present a sliding scale user interface 76 on the display screen 52 that indicate a selected value for a modulation parameter (such as pulse amplitude, pulse width, or pulse rate), or a selected value for the modulation magnitude when the RC 260 is placed in a Modulation Magnitude Adjustment Mode. The sliding scale user interface 76 may additionally include one or more of a perception threshold indicator 78, or a maximum tolerable threshold indicator 90. The perception threshold indicator 78, which may be identified by letters "PT" on the sliding scale user interface 76, may correspond to a perceived paresthesia or other sensations produced by electrostimulation. The maximum tolerable threshold indicator 90, which may be identified by letters "MS", may correspond to strongest stimulation with therapeutic effects yet without causing substantial side-effects. The perception threshold indicator 78 or a maximum tolerable threshold indicator 90 may be determined through an automated testing process, or programmed by a system user such as a clinician. Other than the sliding scale, other textual or graphical representations of the range as defined by the perception threshold indicator 78 or the maximum tolerable threshold indicator 90 and the selected modulation parameter values may be used, which is contemplated by the present inventors and within the scope of the present document.

The sliding scale user interface 76 may be graduated with a scale 92 with units based on a percentage of the perception threshold. In the example as illustrated in FIG. 3A, the scale starts at 0% and increases to 200% of the perception threshold, where the perception threshold is 100%, and the maximum tolerable threshold is around 150%. Via the up/down buttons 60 and 62, a user may selectively increase or decrease the modulation parameter or the modulation magnitude, which may be displayed on the sliding scale user interface 76 as a modulation parameter indicator moving to the left or to the right of the scale. A sub-perception stimulation field may be established when the modulation parameter or the modulation magnitude is set to a value less than 100% (i.e., below the perception threshold), and a supra-perception stimulation field may be established when the when the modulation parameter or the modulation magnitude is set to a value above 100% (i.e., above the perception threshold). The modulation parameter or the modulation magnitude may be adjusted continuously or at pre-determined increment or decrement steps (such as 5% increment or decrement), or be set to one of a plurality of pre-determined levels of stimulation intensity within a specific range such as between the perception threshold indicator 78 and the maximum tolerable threshold indicator 90. In some examples, the perception threshold indicator 78 and the maximum tolerable threshold indicator 90 define a programmable zone within which the patient is allowed to adjust the modulation parameter value or the modulation magnitude. If an attempt is made to program the modulation parameter or the modulation magnitude outside the programmable zone, an alert, in a form of text, graph, sound, or other media formats, may be issued.

In addition to or in lieu of adjusting the modulation parameter or the modulation magnitude relative to the perception threshold "PT", the modulation parameter or the modulation magnitude may be adjusted to a value relative to a baseline electrophysiological measurement, such as local field potential (LCP), evoked compound action potential (ECAP), among other bio-potential measurements. The sliding scale user interface 76 may include the scale 92 with units based on a percentage of the baseline electrophysiological measurement. Via the up/down buttons 60 and 62, a user may increase or decrease the modulation parameter or the modulation magnitude to a level relative to the baseline electrophysiological measurement, and therefore establish a sub-perception or supra-perception stimulation field at a desirable field strength.

FIG. 3B illustrates an RC 260 that includes the selection button 58 that may be actuated to place the RC 260 into a Modulation Program Selection Mode. A plurality of selectable modulation programs may be displayed on the display screen 52, such as modulations programs #1, #2 and #3 illustrated by way of example and not limitation. A user may select a modulation program from the list, or deselect a previously used modulation program, such as via the up/down buttons 60 and 62 or other selection means such as touch-screen selection. Each modulation program may include an aggregation of a plurality of modulation parameters (such as pulse amplitude, pulse width, or pulse rate, among others) with respectively programmed values. Various modulation programs may be associated with different physiological states or physical activity levels. In an example, the selectable modulation programs may include a modulation program for sleep state, a modulation program for awakening state, and a modulation program for a specific physical activity level.

Figure 4:
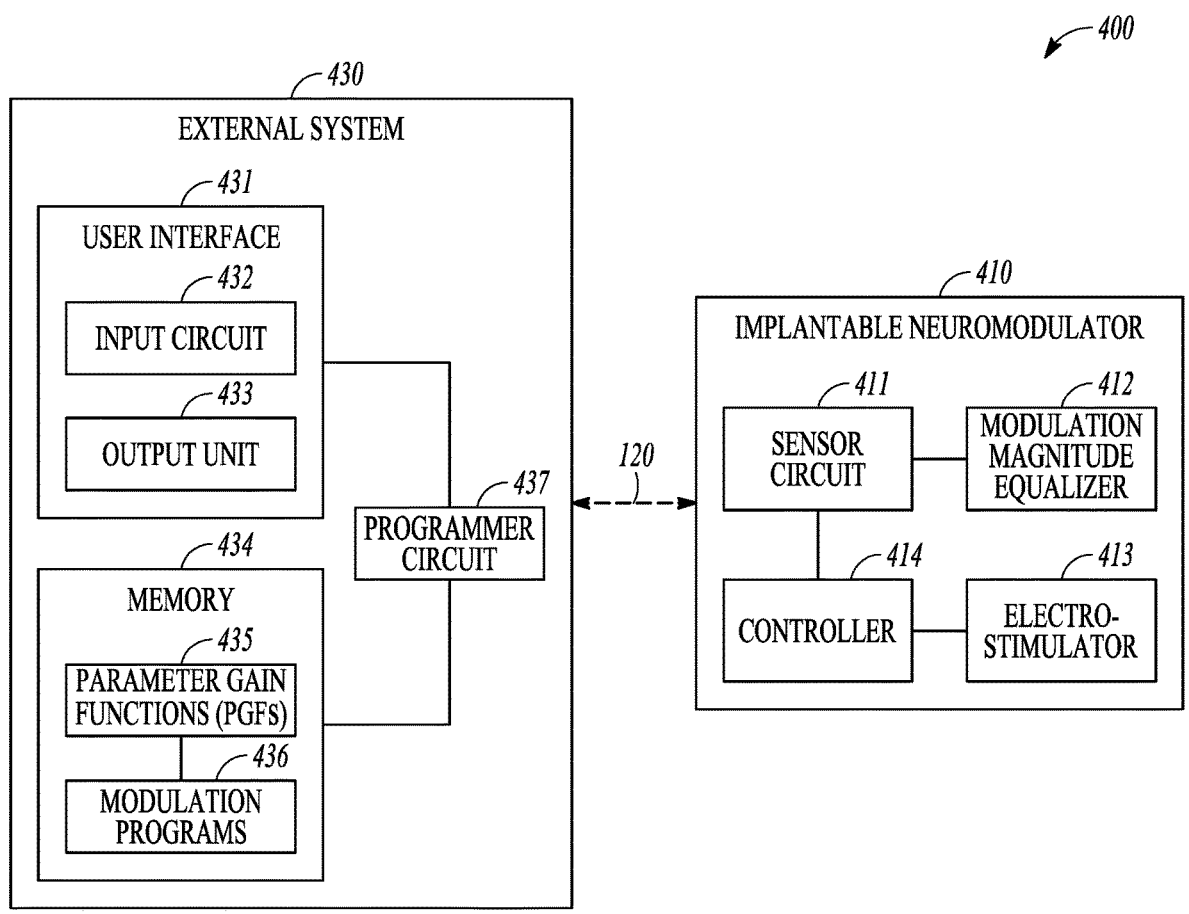
FIG. 4 illustrates, by way of example and not limitation, a neuromodulation system for providing electrostimulation to a patient.

FIG. 4 illustrates, by way of example and not limitation, a neuromodulation system 400 for providing electrostimulation to a patient, which may be an embodiment of the neuromodulation system 100. The neuromodulation system 400 may include an implantable neuromodulator 410 and an external system 430, which are embodiments of the IMD 112 and the external system 130, respectively. The external system 430 may be communicatively coupled to the implantable neuromodulator 410 via the communication link 120.

The implantable neuromodulator 410 may include one or more of a sensor circuit 411, a modulation magnitude equalizer 412, an electrostimulator 413, and a controller 414. The sensor circuit 411 may be coupled to electrodes or various types of ambulatory sensors associated with the patient, and sense physiological or functional signals from the patient. Examples of the physiological signals may include cardiac, hemodynamic, pulmonary, neural, or biochemical signals, among others. Examples of the functional signals may include patient posture, gait, balance, or physical activity signals, among others. In various examples, an accelerometer may be used to detect an activity intensity or activity duration. A tilt switch, an accelerometer, or a thoracic impedance sensor may be used to detect posture or position. Gyroscope, magnetoresistive sensors, inclinometers, goniometers, electromagnetic tracking system (ETS), sensing fabric, force sensor, strain gauges, and sensors for electromyography (EMG) may be used to measure motion and gaits.

The modulation magnitude equalizer 412 may produce a plurality of modulation magnitudes based on the sensed physiological or functional signals. A modulation magnitude may represent stimulation intensity. In an example, the modulation magnitude may be a unit-less number such as from 0 to 10, where "0" indicates no perception of stimulation, and "10" indicates a high and intolerable stimulation intensity. The modulation magnitude equalizer 412 may establish a correspondence between the stimulation intensity (such as at the magnitude of 0 and the magnitude of 10) and a collection of signal metrics generated from the sensed physiological or functional signals. In some examples, the correspondence may additionally include signal metrics of the sensed physiological or functional signals at other intermediate modulation magnitudes, such as between 0 and 10. The established correspondence may be represented as a lookup table, an association map, or other data structures that may be stored in a memory in the implantable neuromodulator. Based on the established correspondence, for a physiological or functional signal is sensed from the patient, a corresponding modulation magnitude may be determined. The modulation magnitude may be forwarded to the external system 430. A system user may determine whether to increase or decrease the modulation magnitude via the user interface 431.

Alternatively, modulation magnitude equalizer 412 may be implemented in the external system 430. The physiological or functional signals sensed from the sensor circuit 411, or the signal metrics generated thereof, may be transmitted to the external system 430. The modulation magnitude equalizer 412 may produce a corresponding modulation magnitude for use in programming the neuromodulation therapy. The implantable neuromodulator 410 may include a communication circuit that enables bi-directional communication between the implantable neuromodulator 410 and the external system 430 via the communication link 120.

The electrostimulator 413 may be configured to generate electrostimulation energy to treat pain or other neurological disorders. In an example, the electrostimulator 413 may deliver spinal cord stimulation (SCS) via electrodes electrically coupled to the electrostimulator 413. The electrodes may be surgically placed at a region at or near a spinal cord tissue, which may include, by way of example and not limitation, dorsal column, dorsal horn, spinal nerve roots such as the dorsal nerve root, and dorsal root ganglia. The SCS may be in a form of stimulation pulses that are characterized by pulse amplitude, pulse width, stimulation frequency, duration, on-off cycle, pulse shape or waveform, temporal pattern of the stimulation, among other stimulation parameters. Examples of the stimulation pattern may include burst stimulation with substantially identical inter-pulse intervals, or ramp stimulation with incremental inter-pulse intervals or with decremental inter-pulse intervals. In some examples, the frequency or the pulse width may change from pulse to pulse. The electrostimulator 413 may additionally or alternatively deliver electrostimulation to other target tissues such as peripheral nerves tissues. The electrostimulator 413 may deliver transcutaneous electrical nerve stimulation (TENS) via detachable electrodes that are affixed to the skin. In another example, the electrostimulator 413 may deliver deep brain stimulation (DBS) via electrodes surgically placed at a brain tissue. In yet another example, the electrostimulator 413 may deliver cardiac or neural stimulation therapy to treat a cardiovascular disease.

The controller 414, coupled to the electrostimulator 413, may control the generation and delivery of the neuromodulation energy. The controller 414 may control the generation of electrostimulation pulses according to specific programming of stimulation parameters, such as provided by the programmer circuit 437 in the external system 430. The stimulation parameters may include temporal modulation parameters such as pulse amplitude, pulse width, pulse rate, or burst intensity, morphological modulation parameters respectively defining one or more portions of stimulation waveform morphology (such as amplitude, pulse width, or other modulation parameters) of different phases or pulses included in a stimulation burst, or spatial modulation parameters such as selection of active electrodes, electrode combinations which define the electrodes that are activated as anodes (positive), cathodes (negative), and turned off (zero), and stimulation energy fractionalization which defines amount of current, voltage, or energy assigned to each active electrode and thereby determines spatial distribution of the modulation field. The controller 414 may control the electrostimulator 413 to generate electrostimulation energy to establish sub-perception or supra-perception stimulation field. In some examples, the controller 414 may control the electrostimulator 413 to generate hybrid electrostimulation that includes simultaneous sub-perception or supra-perception stimulation fields at one or more stimulation sites.

The external system 430 may include a user interface 431, a memory 434, and a programmer circuit 437. The user interface 431 may be associated with either the programmer 180 or the intermediate controller 160 as illustrated in FIG. 1, or be distributed between the programmer 180 and the intermediate controller 160. The user interface 431 may include an input circuit 432 and an output unit 433. The input circuit 432 may enable a system user, such as a clinician or a patient, to provide programming information for one or more modulation parameters. Examples of the input circuit 432 may include a keyboard, on-screen keyboard, mouse, trackball, touchpad, touch-screen, or other pointing or navigating devices such as the selection and navigation buttons 58, 60 and 62 in the intermediate controller 160.

In an example, the input circuit 432 may be configured to receive, such as from a system user, modulation magnitude representing a level of stimulation intensity. As previously discussed, a single modulation magnitude may concurrently control two or more modulation parameters such as the pulse amplitude, pulse width, pulse rate (also known as pulse frequency), burst intensity, or other morphological parameters. In some examples, the input device 432 may be configured to allow user input of the modulation magnitude only within a specific programmable zone, which may be defined by one or both of a lower bound ($M_{min}$) and an upper bound ($M_{max}$). The lower bound $M_{min}$ may be associated with a perception threshold that is sufficient to cause perceived paresthesia or other sensations caused by the electrostimulation. The upper bound $M_{max}$ may be associated with a maximum tolerable threshold with therapeutic effects and without causing substantial side-effects. The lower and upper bounds $M_{min}$ and $M_{max}$ may be graphically identified on the display of the output unit 433, such as the identifiers "PT" or "MS" on the sliding scale user interface 76 of the RC 260, as illustrated in FIG. 3A. An alert may be triggered if a system user attempts to program the modulation magnitude outside the programmable zone.

In some examples, the input device 432 may be configured to allow user input of the modulation magnitude represented by a value relative to a baseline electrophysiological measurement, such as LCP, ECAP, or other biopotential measurements. The modulation magnitude may be set to a percentage of the baseline electrophysiological measurement such as via the RC 260, and establish a sub-perception or supra-perception stimulation field at a desirable field strength. In an example of hybrid electrostimulation where both sub-perception and supra-perception stimulation fields are to be established for stimulation one or more target sites, the input device 432 may be configured to allow user input of a first modulation magnitude relative to a baseline electrophysiological measurement, and a second modulation magnitude relative to a perception threshold "PT". The controller 414 may control the electrostimulator 413 to deliver electrostimulation according to the first modulation magnitude to establish the sub-perception stimulation field, and to deliver electrostimulation according to the second modulation magnitude to establish the supra-perception stimulation field.

The output unit 433 may include a display screen to display information sensed by the implantable neuromodulator 410. This may include the sensed physiological and functional signals, the signal metrics, or the modulation magnitude generated from the modulation magnitude equalizer 412. The information may be presented in a table, a chart, a diagram, or any other types of textual, tabular, or graphical presentation formats, for displaying to a system user. The presentation of the output information may include audio or other human-perceptible media format. In some examples, the modulation magnitude generated from the modulation magnitude equalizer 412 may be presented on the display, and the system user to choose to confirm, reject, or otherwise modify the modulation magnitude before it is used for programming the neuromodulation therapy.

The memory 434 may store a plurality of parameter gain functions (PGFs) 435 {f1,f2, . . . , fN}, respectively defined for a plurality of modulation parameters {X1, X2, . . . , XN}. Each PGF may define a correspondence between values of a modulation parameter Xi and a plurality of modulation magnitudes M. That is, the modulation parameter Xi may be defined as a function (f1) of the modulation magnitude M: Xi=f1(M). The PGFs may be linear, piece-wise linear, or non-linear functions of the modulation magnitude M. As previously discussed, the modulation magnitude M may be represented as a value relative to a perception threshold or relative to a baseline electrophysiological measurement. In an example, the PGF for one modulation parameter (e.g., Xi) may be defined as a function of modulation magnitude M relative to the perception threshold, while the PGF for a different modulation parameter (e.g., Xj) may be defined as a function of modulation magnitude M relative to the baseline electrophysiological measurement. In an example, stored in the memory 434 may include a first PGF (f1) for pulse amplitude $P_A$ where $P_A$=f1(M), a second PGF (f1) for pulse width $P_W$ where $P_W$=f2(M), and a third PGF (f3) for pulse rate $P_R$ where $P_R$=f3(M), and a fourth PGF (f4) for burst intensity $B_I$ where $B_I$=f4(M). Other than the temporal modulation parameters, the PGFs stored in the memory 434 may additionally or alternatively include one or more of morphological modulation parameters or spatial modulation parameters. Examples of the PGFs for modulation parameters are discussed below, such as with reference to FIGS. 5-6.

The programmer circuit 437, which is coupled to the user interface 432 and the memory 434, may generate values for the plurality of modulation parameters based on the modulation magnitude received from the input circuit 432 and the PGFs stored in the memory 434. For example, if a modulation magnitude of M=3 is provided by a system user, values of the modulation parameters {X1, X2, . . . , XN} may be determined according to the respective PGFs, that is, Xi=f1(3), for i=1, 2, . . . , N. The modulation parameter values may be transmitted to the implantable neuromodulator 410 via the communication link 120. The controller 414 of the implantable neuromodulator 410 may program the electrostimulator with the modulation parameters, and control the electrostimulator 413 to elicit the electrostimulation therapy according to the programming of the plurality of modulation parameters.

The programmer circuit 437 may additionally or alternatively select or deselect a modulation program based on the user specified modulation magnitude. As illustrated in FIG. 4, stored in the memory 434 may include modulation programs 436. The modulation programs may be associated with different physiological states or physical activity levels. In an example, the selectable modulation programs may include a first modulation program for sleep state, a second modulation program for awakening state, and a third modulation program for a specific physical activity level. A modulation program may include an aggregation of a plurality of modulation parameters with respectively programmed values. The modulation programs may different from each other by the number or type of modulation parameters. For example, a first modulation program designed for awakening and resting state may have a different modulation waveform (as defined by the temporal modulation parameters) than a second modulation program designed for sleep state, and may have a different electrode combinations or modulation energy fractionalization than a third modulation program designed for a physically active state.

The selected modulation program (including the modulation parameters with respectively programmed values) may be transmitted to the implantable neuromodulator 410, where the controller 414 may program the electrostimulator 413 with the selected modulation program, and control the electrostimulator 413 to elicit the electrostimulation therapy according to the selected modulation program, or to withhold the electrostimulation therapy according to the deselected modulation program.

In various examples, at least some part of the memory 434 and the programmer circuit 437 may be implemented within the implantable neuromodulator 410, such that the determination of the modulation parameter values may be executed within the implantable neuromodulator 410. In an example, personalized PGFs may be created for a particular patient and stored in a memory (not shown) within the implantable neuromodulator 410. The programmer circuit 437, which may also reside within the implantable neuromodulator 410, may receive the modulation magnitude from the input circuit 432 and determine the modulation parameter values according to the PGFs associated with the modulation parameters. Similarly, the modulation programs 436 may be personalized for individual patient and stored in the memory within the implantable neuromodulator 410, and the programmer circuit 437 may determine the modulation program for use in electrostimulation therapy based on the modulation magnitude from the input circuit 432. Transmitting through the communication link 120 the modulation magnitude rather than values of a multitude of modulation parameters may be advantageous in saving on the communication bandwidth. The personalized PGFs may be individually determined or updated according to patient needs or sensor feedback.

FIGS. 5A-5D illustrates, by way of example and not limitation, temporal modulation parameters as controlled by the modulation magnitude and the resulting electrostimulation waveforms. The electrostimulation waveform is created from a base pulse of a biphasic pulse as illustrated in 510A. Various electrostimulation waveforms may be generated by altering and/or repeating the biphasic pulse according to the temporal modulation parameters defined by the respective PGFs. The electrostimulation waveforms may be displayed on a display of the output unit 433, or on the programmer 180 or the intermediate controller 160. Neuromodulation energy may be generated at the electrostimulator 413 in accordance with the electrostimulation waveforms.

The temporal modulation parameters include pulse amplitude (FIG. 5A), pulse rate (also known as pulse frequency, FIG. 5B), and burst intensity (FIG. 5C), each of which is determined as respective PGFs of the modulation magnitude. By way of non-limiting examples, the PGFs for pulse amplitude, pulse rate, and burst intensity in FIGS. 5A-5C are all growth functions of modulation magnitude. As such, the modulation parameters increase proportionally to an increase in the modulation magnitude. The modulation magnitude is represented by a unit-less value between 0 and 10. At a high modulation magnitude of M=10, the electrostimulation waveforms may be characterized by a high pulse amplitude 510A, a high pulse rate 510B, or a high burst intensity 510C. When the modulation magnitude is reduced to a medium high level of M=7, the electrostimulation waveforms may be characterized by a medium high pulse amplitude 520A, a medium high pulse rate 520B, or a medium high burst intensity 520C. As the modulation magnitude is further reduced to a medium low level of M=4, the electrostimulation waveforms may be characterized by a medium low pulse amplitude 530A, a medium low pulse rate 530B, or a medium low burst intensity 530C. Finally at a low modulation magnitude of M=2, the electrostimulation waveforms may be characterized by a low pulse amplitude 540A, a low pulse rate 540B, or a low burst intensity 540C. The temporal modulation parameters, such as pulse amplitude, pulse width, pulse rate, or burst intensity, determine the amount of energy delivered to the target tissue. In accordance with PGFs being growth functions of modulation magnitude, the amount of energy delivered to the tissue and thus the aggressiveness of the electrostimulation therapy may be proportionally controlled by the single parameter of modulation magnitude.

FIG. 5D illustrates concurrent adjustment of more than one modulation parameter, which, by way of example and not limitation, may include both pulse amplitude and burst frequency. Both the PGF for pulse amplitude and the PGF for pulse rate are growth functions of modulation magnitude, such that both the pulse amplitude and the pulse rate would decrease as the modulation magnitude decreases. As illustrated in FIG. 5D, the electrostimulation waveforms 510D, 520D, 530D and 540D are characterized by concurrent decrease in pulse amplitude and pulse rate, corresponding to successively decreasing modulation magnitudes of 10, 7, 4 and 2.

FIGS. 6A-6F illustrates, by way of example and not limitation, morphological modulation parameters as controlled by the modulation magnitude and the resulting electrostimulation waveforms. The morphological modulation parameters may define various portions of the electrostimulation waveform morphology. The electrostimulation waveform may include a base pulse in the form of uni-phasic, biphasic, or multi-phasic pulse, or other user defined pulse shape or morphology. In the examples illustrated in FIGS. 6A-6F, the base pulse is a biphasic waveform including a first pulse 605 and a second pulse 606. Amplitude (A1) of the first pulse 605 is a first PGF (f1) of the modulation magnitude M, and amplitude (A2) of the second pulse 606 is a second PGF (f2) of the same modulation magnitude M, that is, A1=f1(M) and A2=f2(M). In some examples, modulation parameters other than pulse amplitude, such as pulse width or other morphological parameters, may alternatively or additionally be defined for the first and second pulses.

Figure 6A:
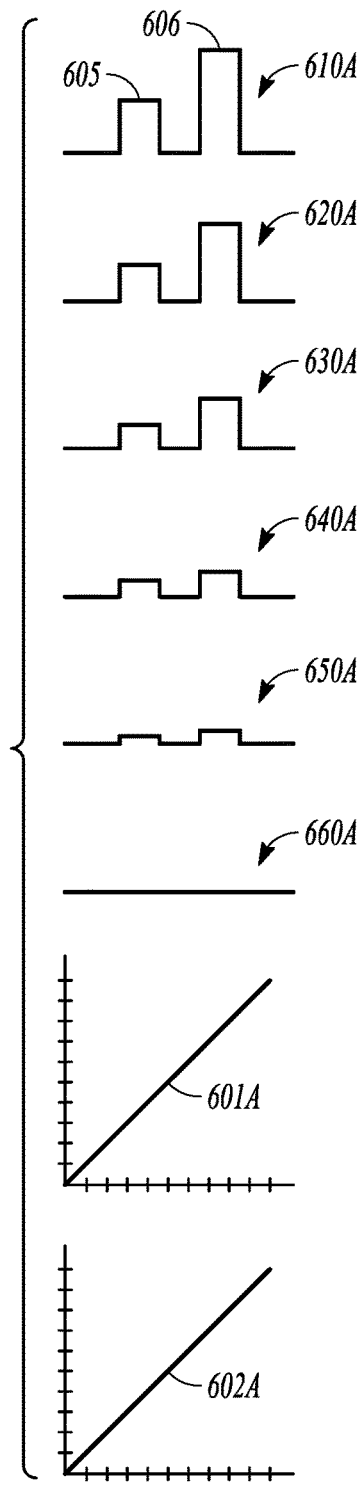
FIGS. 6A-6F illustrates, by way of example and not limitation, morphological modulation parameters as controlled by the modulation magnitude and the resulting electrostimulation waveforms.

The electrostimulation waveforms, including the amplitudes A1 and A2 respectively for the first and second pulses, may be determined by the PGFs (f1 and f2) and the modulation magnitude. In FIG. 6A, the PGFs f1 and f2 (601A and 602A, respectively) are linear growth functions. As such, A1 and A2 both decrease proportionally to the reduction of the modulation magnitude from 100% to 75%, 50%, 25%, 10%, and 0% of the maximal modulation magnitude ($M_{max}$), as shown in respective electrostimulation waveforms 610A-660A.

Figure 6B:
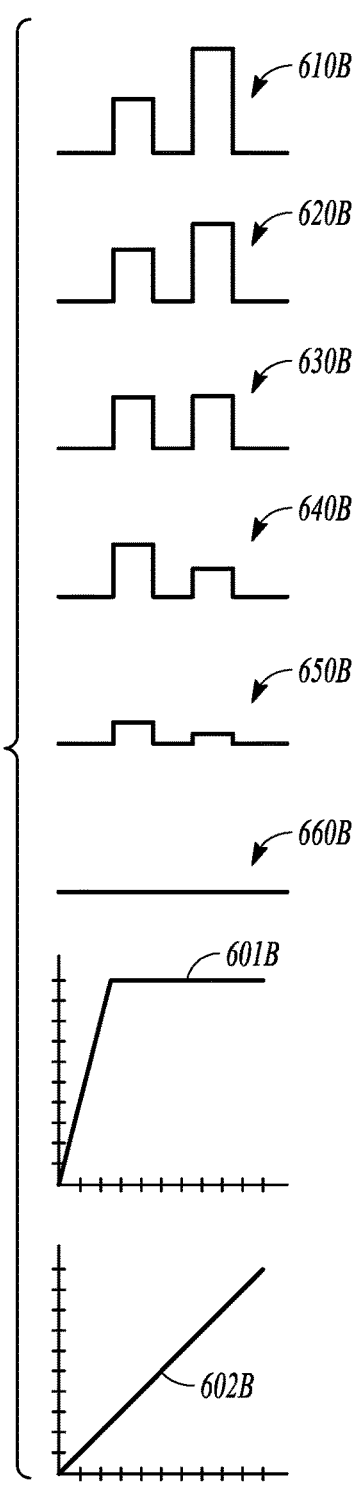

In FIG. 6B, the PGF f2 (602B) is a linear growth function, and the PGF f1 (601B) is a piece-wise linear function with an initial linear growth portion at low M values between 0-25% of $M_{max}$, and a subsequent constant gain when M exceeds 25%*$M_{max}$. As shown in electrostimulation waveforms 610B-660B, when the modulation magnitude changes from 100% to 75%, 50%, 25%, 10%, and 0% of $M_{max}$, A2 decreases proportionally to the reduction of the modulation magnitude. However, A1 of the first pulse remains constant until the modulation magnitude drops below 25%*$M_{max}$, where A1 starts to decrease proportionally to the reduction of the modulation magnitude.

Figure 6C:
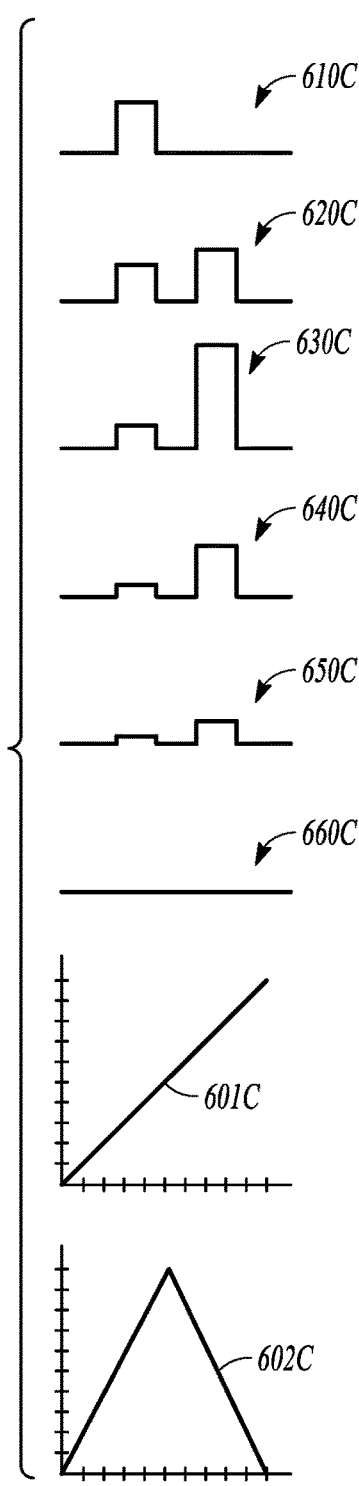

In FIG. 6C, the PGF f1 (601C) is a linear growth function, and the PGF f2 (602C) is a piece-wise linear function, which has an initial linear growth portion at low M values between 0-50%*$M_{max}$, and a subsequent linear decay portion when M exceeds 50%*$M_{max}$. As shown in electrostimulation waveforms 610C-660C, when the modulation magnitude changes from 100% to 75%, 50%, 25%, 10%, and 0% of $M_{max}$, A1 decreases proportionally to the reduction of the modulation magnitude. However, A2 of the second pulse increases proportionally when the modulation magnitude decrease down to 50%*$M_{max}$, at which point A1 begins to decrease proportionally to the reduction of the modulation magnitude.

Figure 6D:
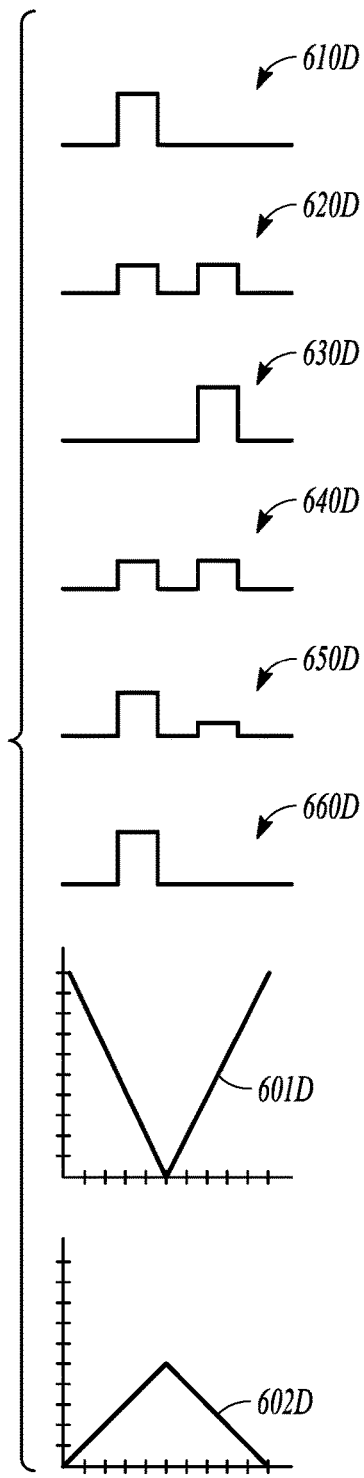

In FIG. 6D, both the PGFs f1 and f2 (601D and 602D, respectively) are piece-wise linear functions. The PGF f1 (601D) comprises an initial linear decay portion at low M values between 0-50%*$M_{max}$, and a subsequent linear growth portion when M exceeds 50%*$M_{max}$. The PGF f2 (602D) comprises an initial linear growth portion at low M values between 0-50%*$M_{max}$, followed by a linear decay portion when M exceeds 50%*$M_{max}$. The maximal gain of A2, which can be reached at 50%*$M_{max}$, is set to about half the base value of A2. As shown in electrostimulation waveforms 610D-660D, when the modulation magnitude changes from 100% to 75%, 50%, 25%, 10%, and 0% of $M_{max}$, A1 decreases proportionally to the reduction of the modulation magnitude until 50%*$M_{max}$ of the modulation magnitude is achieved, at which point A1 then starts to increase proportionally to the reduction of the modulation magnitude. A2 of the second pulse increases proportionally when the modulation magnitude decrease down to 50%*$M_{max}$, and then decreases proportionally to the reduction of the modulation magnitude.

Figure 6E:
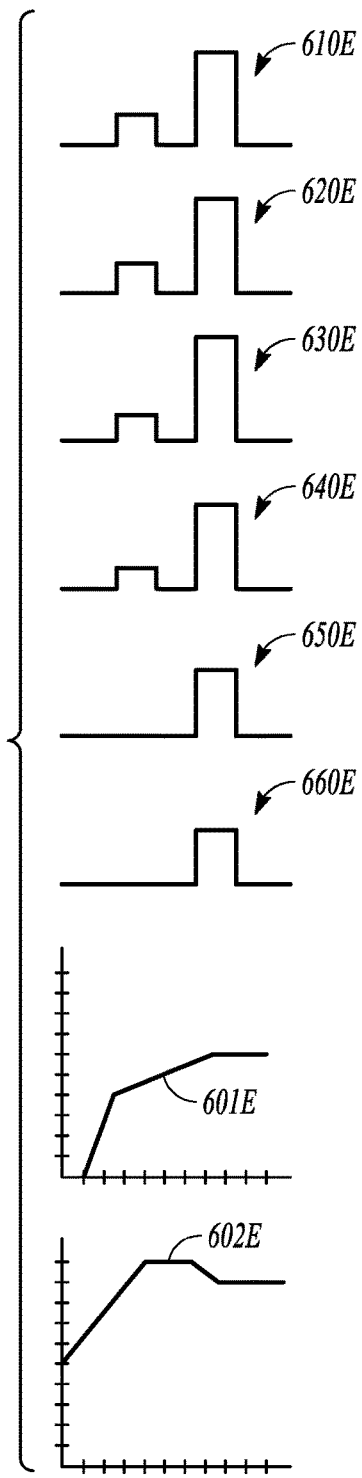

In FIG. 6E, the PGF f1 (601E) comprises four portions corresponding to four consecutive segments of modulation magnitudes between 0-100%*$M_{max}$. The first portion is zero gain such that A1 stays at zero for modulation magnitudes of 0-10%*$M_{max}$. The second portion is a fast linear growth portion where A1 increases from 0 to about 40% of the base amplitude corresponding to modulation magnitudes of 10-25%*$M_{max}$. The third portion is a slow linear growth portion where A1 increases from 40% to about 60% of the base amplitude corresponding to modulation magnitudes of 25-75%*$M_{max}$. The fourth portion is a plateau where A1 maintains at about 60% of the base amplitude when the modulation magnitude exceeds 75%*$M_{max}$. The PGF f2 (602E) also comprises four portions corresponding to four consecutive segments of modulation magnitudes. The first portion is a linear growth portion where A2 increases linearly from about 50% of the base amplitude at the modulation magnitude of 0 to the full base magnitude at the modulation magnitude of 40%*$M_{max}$. The second portion is a plateau where A2 maintains at the full base amplitude for modulation magnitudes of 40-60%*$M_{max}$. The third portion is a linear decay portion where A2 decrease from the full base amplitude to about 90% of the base amplitude corresponding to modulation magnitudes of 60-75%*$M_{max}$. The fourth portion is a plateau where A1 maintains at about 90% of the base amplitude when the modulation magnitude exceeds 75%*$M_{max}$. The electrostimulation waveforms 610E-660E corresponding to various modulation magnitudes at 100% to 75%, 50%, 25%, 10%, and 0% of $M_{max}$ illustrates the A1 and A2 as determined by the PGFs 601E and 602E.

Figure 6F:
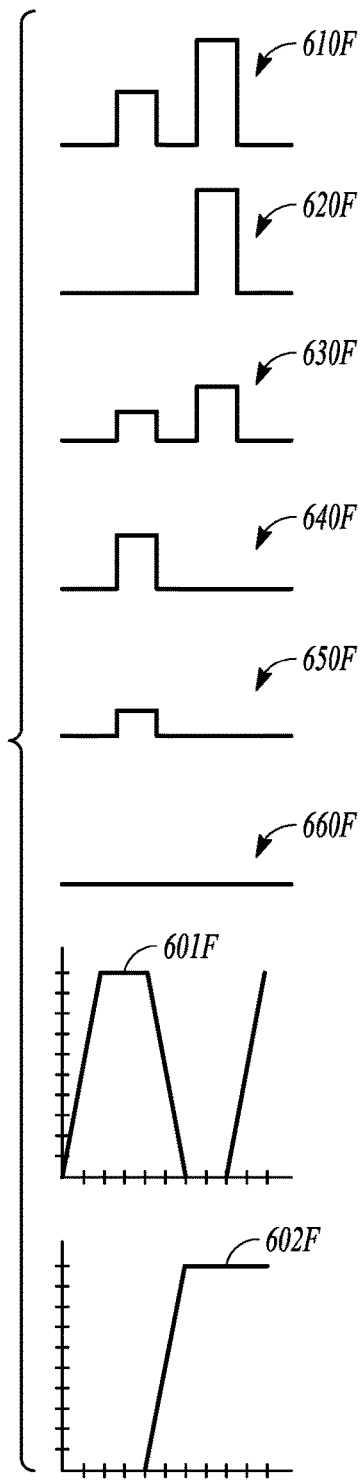

In FIG. 6F, both the PGFs f1 and f2 (601F and 602F, respectively) are piece-wise linear functions. The PGF f1 (601F) comprises five portions corresponding to five consecutive segments of modulation magnitudes between 0-100%*$M_{max}$. The first portion is a linear growth portion where A1 elevates from zero to full base amplitude corresponding to modulation magnitudes of 0-20%*$M_{max}$. The second portion is a plateau where A1 maintains a full base amplitude corresponding to modulation magnitudes between 20-40%*$M_{max}$. The third portion is a linear decay portion where A1 drops from full base amplitude down to zero corresponding to modulation magnitudes of 40-60%*$M_{max}$. The fourth portion is a zero-gain portion where A1 stays at zero for M values between 60-80%*$M_{max}$. The fifth portion, which corresponds to M values between 80-100%*$M_{max}$, includes a linear growth portion where A1 again elevates from zero to full base amplitude. The PGF f2 (602F) comprises an initial portion of zero gain corresponding to modulation magnitudes of 0-40%*$M_{max}$. Subsequently, there is a linear growth portion where A1 elevates from zero to full base amplitude corresponding to modulation magnitudes falling between 40-60%*$M_{max}$. For modulation magnitudes exceeding 60%*$M_{max}$, A2 reaches a plateau at the full base amplitude. The electrostimulation waveforms 610F-660F corresponding to various modulation magnitudes at 100% to 75%, 50%, 25%, 10%, and 0% of $M_{max}$ illustrates the A1 and A2 as determined by the PGFs 601F and 602F.

Figure 7:
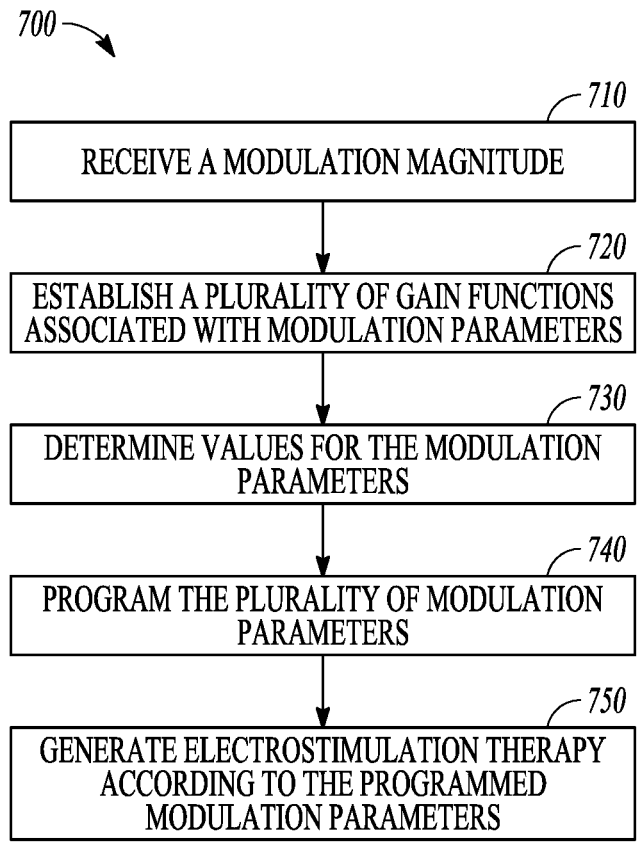
FIG. 7 illustrates, by way of example and not limitation, a method for programming an ambulatory medical device such as an implantable neuromodulation device to provide electrostimulation to a patient.

FIG. 7 illustrates, by way of example and not limitation, a method 700 for programming an ambulatory medical device (AMD) such as an implantable neuromodulation device to provide electrostitnulation to a patient. The method 700 may be used to provide neuromodulation therapy, such as SCS, DBS, PNS, FES, or VNS therapies, to treat pain or various neurological disorders. The method 700 may additionally or alternatively be used to provide electrostimulation therapy to treat a cardiovascular disease or other health disorders.

The method 700 may be implemented in a medical system, such as the neuromodulation system 400. In an example, at least a portion of the method 700 may be executed by an ambulatory device such as the IMD 112, or the implantable neuromodulator 410, among other implantable or wearable devices. In another example, at least a portion of the method 700 may be executed by an external programmer or remote server-based patient management system, such as the external systems 130 or 430 that may be communicatively coupled to the ambulatory device. In some examples, steps included in the method 700 may be distributed between an ambulatory device and an external device in communication with the ambulatory device.

The method 700 begins at step 710, where a modulation magnitude may be received from a system user. The programmer 180 or the intermediate controller 160 as illustrated in FIG. 1, or the RC 260 in FIG. 2, may be used to provide the modulation magnitude. In an example, a user may place the intermediate controller 160 (or RC 260) in a Modulation Magnitude Adjustment Mode, and provide or select an appropriate modulation magnitude using control buttons, dial, slider bar, or other actuators on the RC 260, as illustrated in FIGS. 2 and 3A.

The modulation magnitude represents a level of stimulation intensity. The modulation magnitude may be a unit-less number such as between 0 and 10, where "0" indicates no perception of stimulation, and "10" indicates a high and intolerable stimulation intensity. The modulation magnitude may be associated with two or more modulation parameters such as the pulse amplitude, pulse width, or pulse rate (also known as pulse frequency), such that two or more modulation parameter may be concurrently programmed using a single modulation magnitude. In some examples, the modulation magnitude provided by the system user may be required to be within a specific magnitude range such as defined by one or both of a lower bound ($M_{min}$) and an upper bound ($M_{max}$). The lower bound $M_{min}$ may be associated with a perception threshold that is sufficient to cause perceived paresthesia or other sensations caused by the electrostimulation. The upper bound $M_{max}$ may be associated with a maximum tolerable threshold with therapeutic effects and without causing substantial side-effects. In some examples, the modulation magnitude may be represented by a value relative to a baseline electrophysiological measurement, such as LCP, ECAP, or other bio-potential measurements. In various examples, a first modulation magnitude relative to a baseline electrophysiological measurement may be used to establish a sub-perception stimulation field, and a second modulation magnitude relative to a perception threshold "PT" may be used to establish a supra-perception stimulation field. The sub-perception and supra-perception stimulation may be delivered simultaneously according to a hybrid electrostimulation program.

At 720, a plurality of parameter gain functions (PGFs) associated with respective modulation parameters may be established. Each PGF may define a correspondence between values of a modulation parameter and modulation magnitudes. In an example, the PGFs may be individually and independently defined for the respective modulation parameters, including but not limited to PGFs for pulse amplitude, pulse width, pulse rate, burst intensity, pulse morphological parameters, or electrode combination and energy fractionalization, such as the as illustrated in FIGS. 5A-5D. In another example, the PGFs may be defined for various portions of an electrostimulation waveform morphology, including but not limited to PGFs for various phases of a bi-phasic or multi-phasic electrostimulation waveform, such as the PGFs as illustrated in FIGS. 6A-6F. The PGFs may be may be linear, piece-wise linear, or non-linear functions. In an example, a PGF or a portion of the PGF may be a linear or nonlinear growth function of a modulation parameter, such that an increase in the modulation magnitude would result in proportional increase in the modulation parameter. In another example, a PGF or a portion of the PGF may be a linear or nonlinear decay function of a modulation parameter, such that an increase in the modulation magnitude would result in proportional decrease in the modulation parameter. The PGFs thus created may be stored in a memory such as within the programmer 180 or the intermediate controller 160, and can be retrieved upon a request command.

At 730, values for the modulation parameters may be determined according to the respective PGFs at the specific modulation magnitude. The modulation parameter values may be determined by the programmer circuit 437 such as implemented within the programmer 180, as illustrated in FIG. 4. A740, the modulation parameter values thus determined may be used to program an electrostimulator such as included within the implantable neuromodulator 410 or within the IMD 112. Electrostimulation energy may be generated at 750 according to the programmed modulation parameters. The electrostimulation energy may be used to treat chronic pain or other neurological disorders or cardiovascular disease. In an example, spinal cord stimulation (SCS) may be delivered via electrodes surgically placed at a region at or near a spinal cord tissue. In another example, transcutaneous electrical nerve stimulation (TENS) may be delivered via detachable electrodes affixed to the skin. In yet another example, deep brain stimulation (DBS) may be delivered via electrodes surgically placed at a brain tissue. In some examples, cardiac or vagal nerve stimulation may be delivered to treat a cardiovascular disease such as heart failure.

In some examples, the method 700 may be used to select or deselect a modulation program based at least on the user specified modulation magnitude as provided at 710. A modulation program may include an aggregation of a plurality of modulation parameters with respectively programmed values. The modulation programs may be associated with different physiological states or physical activity levels. In an example, the selectable modulation programs may include a first modulation program for sleep state, a second modulation program for awakening state, and a third modulation program for a specific physical activity level. Various modulation programs may include different number or different type of modulation parameters, which may be selected from temporal modulation parameters such as pulse amplitude, pulse width, pulse rate, or burst intensity, morphological modulation parameters respectively defining one or more portions of stimulation waveform morphology such as amplitude of different phases or pulses included in a stimulation burst, or spatial modulation parameters such as selection of active electrodes, electrode combinations, stimulation energy fractionalization (such as current or voltage distribution) over the selected active electrodes which determines the spatial distribution of the modulation field.

For each modulation program, PGFs for the modulation parameters associated with that modulation program may be established at 720. PGFs in one modulation program may be different than the PGFs in another different modulation program. For example, a modulation program for resting state may include electrostimulation with different waveform morphology or electrode configuration than a modulation program for a physically active state. The user specified modulation magnitude as provided at 710 may then be used to select a modulation program, and the values for the modulation parameters associated with the selected modulation program may be determined at 730. The electrostimulator may then be programmed at 740 with the selected modulation program, and electrostimulation energy may be generated at 750 according to the selected modulation program. In some examples, an existing modulation program may be deselected at 730, and the electrostimulation therapy according to the deselected modulation program may be withheld from being delivered to the patient.

In some examples, the method 700 may be used to modify an existing electrostimulation therapy such as by adjusting the modulation magnitude at 710 and/or updating the PGFs for one or more modulation parameters or a modulation program at 720. In an example, the adjustment of the modulation magnitude and/or the update of one or more PGFs may be based on patient physiological or functional response to the delivery of electrostimulation therapy which may be sensed using sensors configured to sense physiological or functional signals from the patient. If the physiological or functional response satisfies a specified condition such as reduction of pain symptom or improved neurological or cardiovascular function, the existing electrostimulation therapy is deemed effective. Otherwise, a feedback-control of therapy may be initiated. By way of example and not limitation, in a closed-loop pain management system, if an existing pain therapy does not effective relieve the pain, then the modulation magnitude may be increased at 710 to increase the perceived therapy intensity such as by increasing the amount of energy delivery. Additionally or alternatively, the PGFs for one or more modulation parameters or a modulation program may be updated at 720, such as by increasing one or more of pulse amplitude, pulse width, or pulse rate; configuring different pulse morphology; or reconfiguring the electrode combination such as selecting different active electrodes and redistributing the energy fractionalization.

The above detailed description includes references to the accompanying drawings, which form a part of the detailed description. The drawings show, by way of illustration, specific embodiments in which the invention may be practiced. These embodiments are also referred to herein as "examples." Such examples may include elements in addition to those shown or described. However, the present inventors also contemplate examples in which only those elements shown or described are provided. Moreover, the present inventors also contemplate examples using combinations or permutations of those elements shown or described.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments may be used, such as by one of ordinary skill in the art upon reviewing the above description. The scope of the invention should be determined with reference to the appended claims, along with the full scope of equivalents to which such claims are entitled.

What is claimed is:

1. A method for providing electrostimulation to a patient via an ambulatory medical device (AMD) communicatively coupled to an external programmer device, the method comprising:
    receiving, via the external programmer device, a single user input corresponding to a modulation magnitude;
    determining, by the external programmer device, respective values for a plurality of modulation parameters based on the received single user input of the modulation magnitude; and
    providing, via the AMD, an electrostimulation therapy to the patient in accordance with the determined respective values for the plurality of modulation parameters.

2. The method of claim 1, wherein determining the respective values for the plurality of modulation parameters includes using a plurality of gain functions each defining a correspondence between a modulation parameter and the modulation magnitude.

3. The method of claim 1, wherein determining the respective values for the plurality of modulation parameters includes using a plurality of lookup tables each defining a correspondence between a modulation parameter and the modulation magnitude.

4. The method of claim 1, wherein the plurality of modulation parameters includes at least a temporal modulation parameter and a spatial modulation parameter.

5. The method of claim 4, wherein the temporal modulation parameter includes at least one of a stimulation amplitude, a width of stimulation waveform, a stimulation rate, a duty cycle, or a burst intensity.

6. The method of claim 4, wherein the spatial modulation parameter includes at least one of an election of an active electrode, an electrode combination activate as an anode, an electrode combination activated an cathode, a turned-off electrode, or a stimulation energy fractionalization over a number of electrodes.

7. The method of claim 4, wherein:
the temporal modulation parameter includes a stimulation amplitude, the stimulation amplitude being a growth function of the modulation magnitude; and
the spatial modulation parameter includes a stimulation energy fractionalization representing a size of a modulation field, the size of the modulation field is a growth function of the modulation magnitude.

8. The method of claim 1, wherein the plurality of modulation parameters includes at least a first modulation parameter for modulating sub-perception stimulation and a second modulation parameter for modulating supra-perception stimulation.

9. The method of claim 8, wherein the received single user input of the modulation magnitude is relative to a baseline electrophysiological measurement.

10. The method of claim 8, wherein the received single user input of the modulation magnitude is relative to a perception threshold.

11. The method of claim 8, comprising receiving user input of a first and second modulation magnitudes, wherein:
determining the respective values for the plurality of modulation parameters includes determining a first value for the first modulation parameter based on the received first modulation magnitude, and determining a second value for the second modulation parameter based on the received second modulation magnitude; and
providing the electrostimulation therapy includes providing a sub-perception stimulation in accordance with the first modulation parameter taking the first determined value, and providing a supra-perception stimulation in accordance with the second modulation parameter taking the second determined value.

12. The method of claim 11, wherein the first modulation magnitude is represented by the perception threshold scaled by a first factor less than 100%, and the second modulation magnitude is represented by the perception threshold scaled by a second factor greater than 100%.

13. The method of claim 12, wherein the second modulation magnitude takes a value between the perception threshold and a maximum tolerable threshold.

14. The method of claim 8, wherein providing the sub-perception stimulation includes:
providing a first sub-perception stimulation in accordance with the first modulation parameter taking a value based on a perception threshold scaled by a first factor less than 100%; and
providing a second sub-perception stimulation in accordance with the first modulation parameter taking a value based on a perception threshold scaled by a second factor less than 100%, the second factor different from the first sub-threshold factor.

15. A system for providing electrostimulation to a patient, the system comprising:
an external programmer device configured to receive a single user input corresponding to a modulation magnitude;
a memory configured to store a correspondence between values of a modulation parameter and values of the modulation magnitude;
a controller configured to determine respective values for a plurality of modulation parameters based on the received single user input of the modulation magnitude and the stored correspondence; and
an electrostimulator configured to generate an electrostimulation therapy for delivery to the patient in accordance with the determined respective values for the plurality of modulation parameters.

16. The system of claim 15, wherein the plurality of modulation parameters includes at least a temporal modulation parameter and a spatial modulation parameter.

17. The system of claim 16, wherein:
the temporal modulation parameter includes a stimulation amplitude, the stimulation amplitude being a growth function of the modulation magnitude; and
the spatial modulation parameter includes a stimulation energy fractionalization representing a size of a modulation field, the size of the modulation field is a growth function of the modulation magnitude.

18. The system of claim 15, wherein the plurality of modulation parameters includes at least a first modulation parameter for modulating sub-perception stimulation and a second modulation parameter for modulating supra-perception stimulation.

19. The system of claim 18, wherein:
the external programmer device is configured to receive a first and second modulation magnitudes;
the controller is configured to determine a first value for the first modulation parameter based on the received first modulation magnitude, and determining a second value for the second modulation parameter based on the received second modulation magnitude; and
the electrostimulator is configured to generate a sub-perception stimulation in accordance with the first modulation parameter taking the first determined value, and to generate a supra-perception stimulation in accordance with the second modulation parameter taking the second determined value.

20. The system of claim 15, comprising an implantable device that includes the electrostimulator, wherein the controller is included in the external programmer device or the implantable device.

* * * * *